United States Patent [19]

Swinkels et al.

[11] Patent Number: 4,701,838
[45] Date of Patent: Oct. 20, 1987

[54] CHARACTERIZING AND HANDLING MULTI-COMPONENT SUBSTANCES

[75] Inventors: Dominicus A. Swinkels, Adamstown Heights; Peter M. Fredericks, Hamilton South; Paul R. Osborn, Cooranbong, all of Australia

[73] Assignee: The Broken Hill Proprietary Co., Ltd., Melbourne, Australia

[21] Appl. No.: 692,886

[22] PCT Filed: May 11, 1984

[86] PCT No.: PCT/AU84/00083
§ 371 Date: Dec. 26, 1984
§ 102(e) Date: Dec. 26, 1984

[87] PCT Pub. No.: WO84/04594
PCT Pub. Date: Nov. 22, 1984

[30] Foreign Application Priority Data
May 12, 1983 [AU] Australia .............................. PF9312

[51] Int. Cl.$^4$ ...................... G01N 21/35; G01N 33/24
[52] U.S. Cl. .................................... 364/164; 364/498; 364/502; 201/1; 201/4
[58] Field of Search ............... 364/164, 497, 498, 499, 364/501, 502; 201/1, 4

[56] References Cited
U.S. PATENT DOCUMENTS
4,370,201 1/1983 Lowenhaupt ........................ 201/24

Primary Examiner—Jerry Smith
Assistant Examiner—Allen MacDonald
Attorney, Agent, or Firm—Murray and Whisenhunt

[57] ABSTRACT

A method of handling, as bulk material, a substance which is one member of a class of multi-component substances includes subjecting successive test samples of the substance to a series of measurements which provide multiple data points which are influenced by at least one selected parameter and from which are determined the factor loadings for the respective test sample of each of multiple pre-determined abstract factors. Pre-determined regression coefficients are utilized to calculate from the factor loadings a predicted value for the selected parameter for the respective test sample. The predicted value is compared with one or more related set points, and the constitution and/or disposition of the substance is controlled in response to the outcome of the successive comparisons. The regression coefficients have been determined by correlating known values of the selected parameter for standard characterized samples of each of multiple substances of the class, with factor loadings derived by factor analysis of multiple data points which were obtained by subjecting the standard characterized samples to the series of measurements.

15 Claims, 5 Drawing Figures

CHARACTERIZING AND HANDLING MULTI-COMPONENT SUBSTANCES

FIELD OF THE INVENTION

This invention relates to the characterizing of a multi-component substance, for facilitating assessment of the utility of the substance, and to the handling of such substances in bulk form.

By "multi-component substance" is meant herein those substances which have more than one molecular species and have properties determined by the sum of constituent components, such as chemical and structural components. In this context, different crystal structures of the same molecule constitute distinct molecular species. Typically, the relative proportions of the components would vary and indeed the substance to be characterized, and perhaps handled, would normally be one member of a large set of multi-component substances having identifiable common properties and a generic name, conveniently referred to herein as a "class", for example coal, shale, oil, soil, ores of specific metals, plant or animal tissues, glass, rubber, plastics, paints, pharmaceuticals and specific classes of foodstuffs.

For purposes of explanation, the application of the invention to the analysis of coal, utilizing Fourier transform infrared (FTIR) spectroscopic measurements, will be described in some detail but it is to be understood that the invention has much wider significance both as regards the class of substance analysed and the technique of measurement

BACKGROUND TO THE INVENTION

The characterization of a multi-component substance, for facilitating assessment of the utility of the substance or for handling of the substance (e.g. by way of blend control or sorting), is typically by reference to the values of a number of parameters selected in accordance with the intended utility. To date, it has been necessary to apply a wide range of analytical or other techniques to determine the values of the selected parameters For example, in the case of coal, where exact characterization has become essential to ensure tight control over raw materials for highly sensitive end-use processes, it is necessary by separate experiment to determine the carbon, hydrogen, oxygen, nitrogen and sulphur contents and the volatile components of the organic material in the coal, as well as the inorganic constituents which make up the mineral matter or ash of the coal. Moreover, physical properties such as the specific energy of the coal, the reflectance of the vitrinite components, and the grindability of the coal are each normally determined by separate techniques. As a result, the full characterization of a coal sample for the purpose of quality control or blend control, or for determining its suitability for a particular process, has traditionally required several instrumental techniques and several samples to be treated by these techniques, as well as a significant number of well trained staff to operate each of the different techniques. Furthermore, the time taken to determine the value of each selected parameter is significant and can often extend over at least several days.

By way of further example in the case of metal ores, the determination of the battery activity of manganese ore, necessary because only ore exhibiting high battery activity is suitable for certain applications, presently requires the manufacture and discharge of a small sample battery: a task which takes at least 24 hours per sample.

SUMMARY OF THE INVENTION

It is an objective of the invention to provide a method by which a multi-component substance may be characterized, for facilitating assessment of the utility of the substance and/or handling of the substance, in a manner which obviates the need for multiple analytical techniques in relation to the respective parameters.

In one aspect, the invention entails a novel extension of the techniques of factor analysis, with surprising effects in terms of correlation and predictability. In accordance with the invention, the factor loadings, obtained by factor analysis of a large set of data points obtained from measurements on multiple standard samples, are correlated directly with known values of selected parameters of the samples, for example by multiple linear regression. Such parameters may be, e.g. physical properties and/or chemical compositions. It is surprisingly found that good correlations can be established, and it is then possible to use the derived regression coefficients to calculate reliable predicted values of the respective parameters for unknown samples. As a result, it is possible to greatly reduce the number of expensive instruments, the number of trained operators, and the time required to characterise unknown samples.

The invention accordingly provides, in a first aspect, a method of characterizing a substance, being one member of a class of multi-component substances, by reference to at least one selected parameter, for facilitating assessment of the utility of the substance, comprising:

subjecting a test sample of the substance to a series of measurements which provide multiple data points influenced by the selected parameter(s), and determining from the data points the factor loadings for the test sample of each of multiple pre-determined abstract factors; and utilizing pre-determined regression coefficients to calculate from said factor loadings a predicted value for one or more selected parameters thereby to characterize the substance of the test sample and so facilitate an assessment of the utility of the substance;

wherein said regression coefficients have been determined by correlating known values of one or more selected parameters for standard characterized samples of each of multiple substances of said class, with factor loadings derived by factor analysis of multiple data points which were obtained by subjecting the standard characterized samples to said series of measurements, and wherein said abstract factors are those derived by said factor analysis.

The invention also affords apparatus for characterizing a substance, being one member of a class of multi-component substances, by reference to at least one selected parameter, for facilitating assessment of the utility of the substance, comprising:

measurement means to subject a test sample of the substance to a series of measurements which provide multiple data points influenced by the selected parameter(s);

means to determine from the data points the factor loadings for the test sample of multiple pre-determined abstract factors;

means storing pre-determined regression coefficients; and means to utilize said regression coefficients to calculate from said factor loadings a predicted value for one more selected parameters, whereby to characterize the substance of the test sample and so facilitate an assessment of the utility of the substance;

wherein said regression coefficients have been determined by correlating known values of one or more selected parameters for standard characterized samples of each of multiple substances of said class, with factor loadings derived by factor analysis of multiple data points which were obtained by subjecting the standard characterized samples to said series of measurements, and wherein said abstract factors are those derived by said factor analysis.

The series of measurements to which the test sample and the standard samples are subjected may comprise continuous or discontinuous measurements obtained by various spectroscopy methods, for example visible, infra-red or Fourier transform infrared spectroscopy, by X-ray diffraction, or by nuclear magnetic resonance (NMR) or other methods which provide a large number of measurements which vary with the chemical and/or structural make-up of the samples.

The class of multi-component substances will typically comprise substances having substantial similarities and may be selected from the group including coal, shale, oil, soil, ores of specific metals, plant or animal tissues, glass, rubber, plastics, paints, pharmaceuticals and specific classes of foodstuffs. It will be appreciated that test samples which differ significantly from the standard samples will generally produce a result which is not entirely satisfactory, for example, the properties of a brown coal will not generally be estimated correctly when the abstract factors and regression coefficients used were determined from a group of coking coals.

Said determining storing and utilizing means may comprise a programmed computer.

In a further aspect, the invention affords a method of handling, as bulk material, a substance which is one member of a class of multi-component substances have identifiable common properties, comprising:

subjecting successive test samples of the substance to a series of measurements which provide multiple data points influenced by at least one selected parameter;

determining from the data points the factor loadings for the respective test sample of each of multiple pre-determined abstract factors;

utilizing pre-determined regression coefficients to calculate from said factor loadings a predicted value for the or each selected parameter for the respective test sample;

comparing the or each predicted value with one or more related set points; and controlling the constitution and/or disposition of the substance in response to the outcome of the successive said comparisons;

wherein said regression coefficients have been determined by correlating known values of one or more selected parameters for standard characterized samples of each of multiple substances of said class, with factor loadings derived by factor analysis of multiple data points which were obtained by subjecting the standard characterized samples to said series of measurements, and wherein said abstract factors are those derived by said factor analysis.

In its further aspect, the invention also provides apparatus for handling, as bulk material, a substance which is one member of a class of multi-component substances have identifiable common properties, comprising:

means to subject successive test samples of the substance to a series of measurements which provide multiple data points influenced by at least one selected parameter;

means to determine from the data points the factor loadings for the respective test sample of each of multiple pre-determined abstract factors;

means storing predetermined regression coefficients;

means to utilize said regression coefficients to calculate from said factor loadings a predicted value for one or more selected parameters for the respective test sample;

means to compare one or more predicted values with one or more related set points;

means coupled to and responsive to said comparison means for controlling the constitution and/or disposition of the substance;

wherein said regression coefficients have been determined by correlating known values of one or more selected parameters for standard characterized samples of each of multiple substances of said class, with factor loadings derived by factor analysis of multiple data points which were obtained by subjecting the standard characterized samples to said series of measurements, and wherein said abstract factors are those derived by said factor analysis.

Said test samples may be overlapping, juxtaposed or spaced apart, and may be portions of a stream of the substance or may be diverted samples.

In one particular application, the invention may be applied to the characterization or handling of a coal or metal ore of unknown composition and properties, utilizing one or more Fourier transform infrared (FTIR) spectra as the aforesaid series of measurements. In the case of coal, the selected parameters characterizing the coal may comprise, for example, mean maximum vitrinite reflectance, volatile matter content, hydrogen content, fluidity and Hardgrove grindability index.

It is believed that the method of the invention has particular utility where the information obtained from the measurements and the desired parameters to be determined are both strongly related to a common set of fundamental chemical and structural constituents of the substance, although such relationship may not be apparent, and there may be no obvious direct relationship between the measurement technique and the parameters. The accuracy and precision of the predicted value of a desired parameter depends upon the strength of these relationships and upon the range of standard samples which have been used to derive the regression coefficients.

The accuracy and precision of the derivation of the regression coefficients may be improved by examining which of the many data points obtained by the series of measurements have the highest information content with respect to the parameter of interest and which measurements contribute noise. Those measurements which contribute more noise than information may then be discarded before factor analysis is undertaken. In general terms, all measurements may be weighted in importance in proportion to the sign and magnitude of their information to noise ratio with respect to the parameter of interest before factor analysis is undertaken. Similarly, the abstract factors and associated loadings may be examined for information to noise ratio with respect to each of the parameters of interest and may be discarded and eliminated from the analysis process and/or the regression progress.

BRIEF DESCRIPTION OF THE DRAWINGS

The invention will be further described, by way of example only, with reference to the accompany drawings, in which.

DETAILED DESCRIPTION OF THE DRAWINGS

Figure 1:
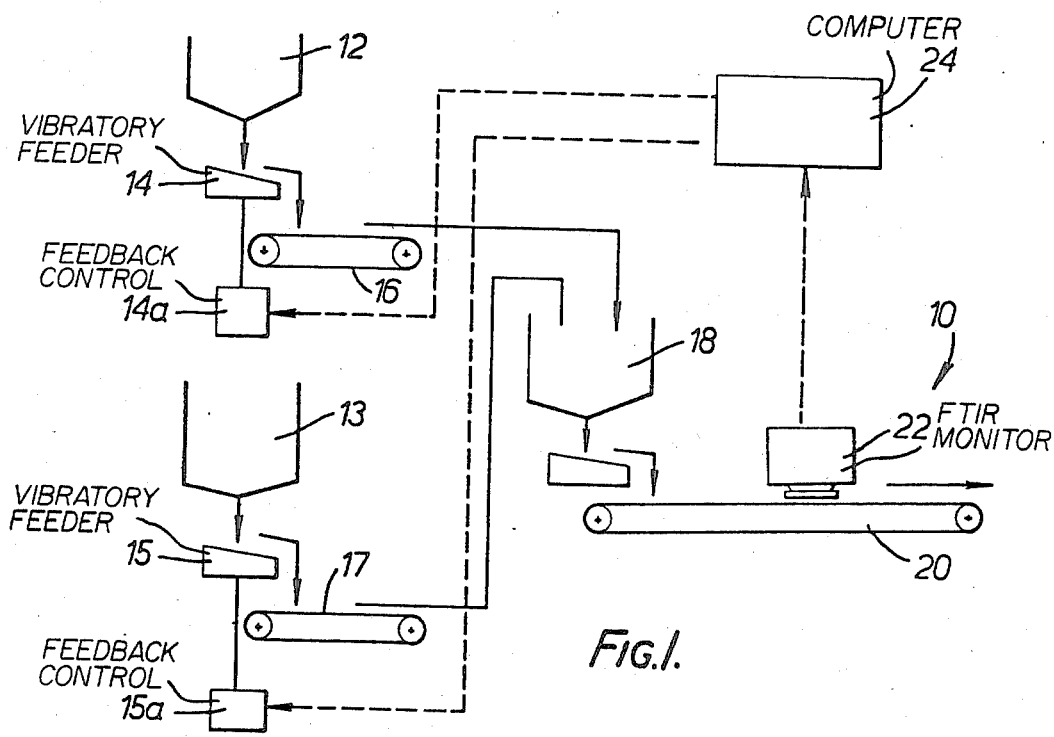
FIG. 1 is a diagram of iron ore blending plant in accordance with the invention.

By way of introduction to FIG. 1, it is noted that iron ore is often sold on the basis of its iron (Fe) content. If the Fe content falls below a specified level, penalty payments are incurred. If, however, the iron content rises significantly above the specified level, then valuable material is shipped without the supplier receiving payment. It is thus important to blend iron ore to a specified Fe content.

FIG. 1 schematically depicts a typical blending arrangement 10 for obtaining, e.g. a 62% Fe blend. Low grade and high grade ores (respectively 55–60% and 60–65% Fe) are delivered from respective hoppers 12, 13 via vibratory feeders 14, 15 and separate belt conveyors 16, 17 to blending plant comprising a hopper 18. The blend is periodically scanned by an FTIR monitor 22 as it is carried away on a further belt conveyor 20. The monitor output is delivered to a process control computer 24 which, in accordance with the invention, derives successive predictions of the Fe content of the blend. The information is compared by the computer with programmed set points and, responsively to this comparison, used for feed back control 14a, 15a of feeders 14, 15 to control in turn the relative proportions of the two grades of ore in the blend. Thus, successive test samples of the blend, comprising FTIR- scanned portions, give rise to successive comparisons in response to which the proportions are controlled. In general, the test samples may be overlapping, juxtaposed or spaced apart, and may be samples diverted from the conveyed stream: the monitoring may be continuous or at intervals.

A suitable FTIR monitor 22 is a Nicolet MX-1E FTIR spectrometer. Computer 24 is conveniently a Hewlett Packard HP 1000 series F minicomputer, operating in FORTRAN 77 under RTE-6/VM, but advances in microcomputer technology may allow programs to be run in very much smaller and cheaper computers. About 400 kilobytes of RAM and 2 megabytes of hard disk are required for a calibration set of up to 200 samples. If the factor analysis is carried out on a separate computer, then only the correlation equations need be stored, together with a program for determining factor loadings of spectra of unknown samples. In this case a microcomputer with about 256 kilobytes of RAM is required. Thus, for implementation of the factor analysis method, a small FTIR spectrometer, or possibly a dispersive instrument equipped with digital calibration output, together with a relatively inexpensive microcomputer will be sufficient for many quality control applications. Sample sets for calibration may be broad, in order to provide semi-quantitative information about widely different samples, or may be restricted in order to give quantitative results of comparable quality to that of conventional methods on more consistent sample sets. The chief advantage of the method is that a number of properties can be estimated simultaneously in the time taken to obtain an FTIR spectrum and to process the data.

Figure 2:
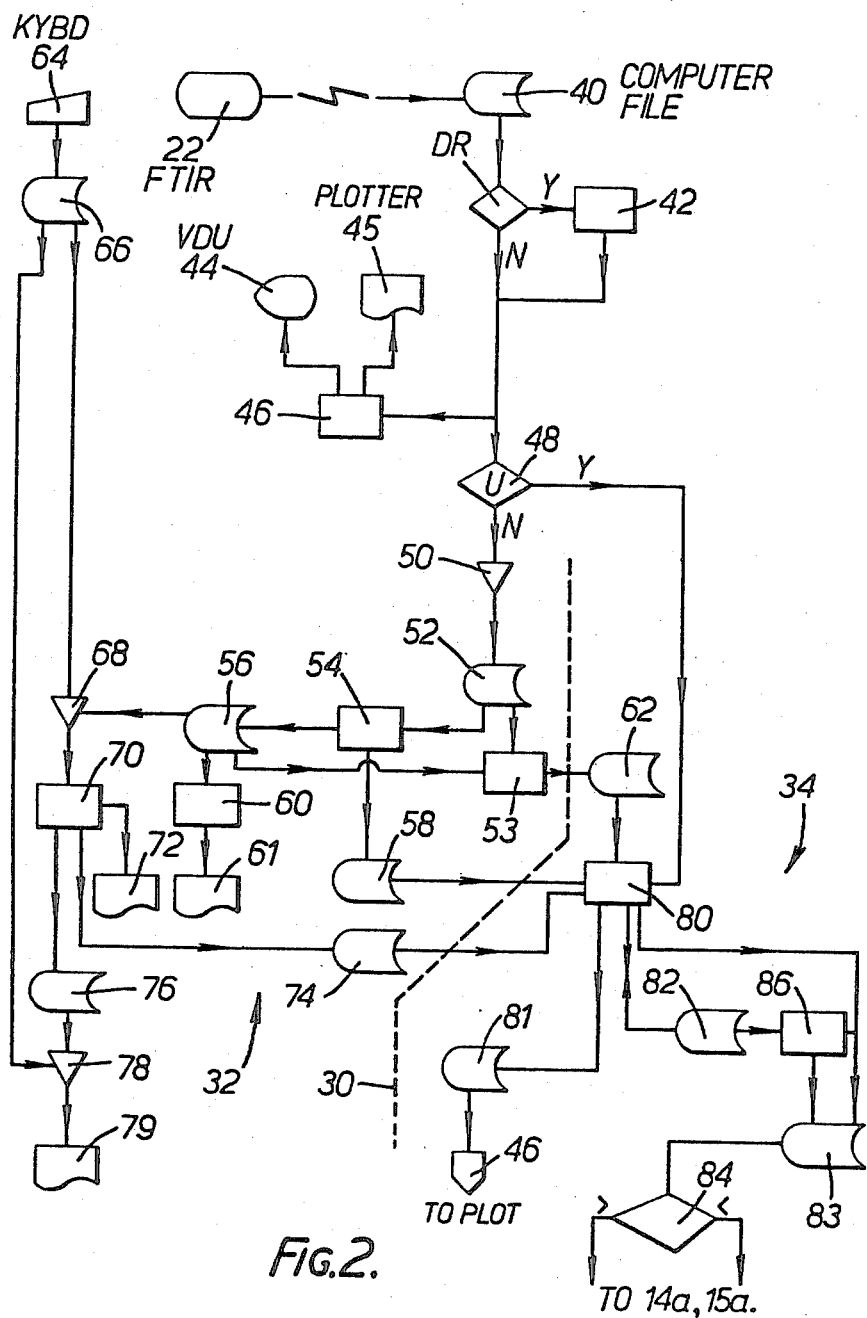
FIG. 2 is a flow chart setting forth both the principal and preferred steps of the inventive process.

The FTIR spectra obtained by monitor 22 are analysed, and the Fe content predicted, in accordance with the flow chart set out in FIG. 2. The chart is partially divided into two segments by dot-dash line 30: segment 32 is preliminary analysis utilizing the FTIR spectra of standard characterized samples of each of multiple substances of the relevant class, in this case the class of iron ores. Segment 34 examines the successive spectra for the unknown ore (the blend passing monitor 22) and utilizes results from the preliminary analysis to derive a predicted value, a good estimate, of Fe content for the blend.

Referring to FIG. 2, for the preliminary analysis, spectra of standard blends, are transferred from the FTIR instrument to disk files (40) in ASCII format. If diffuse reflectance (DR) rather than transmission spectra are obtained, they are treated by program 42 to linearize the spectra. Spectra may be plotted on a visual display unit (44) and/or plotter (45) using program 46. Step 48 directs standard sample spectra for merging by program 50 and storage in a random access binary data file 52.

The contents of file 52 are subject to a factor analysis by program 54 which can select subsets of the data and which produces two output files—factor loadings (56) and the inverses of the primary eigenvalues (58). File 56 is read by a program 60 which outputs a Mahalanobis distance statistic 61 from each sample in the calibration set. These are used to identify samples with a high degree of uniqueness, which can then be eliminated from the factor analysis. File 56 is also utilized, along with original data file 52, to produce (53) a file 62 containing the derived abstract factors.

The measured values of various properties for the standard characterized samples, the calibration set, including particular selected property in this case, Fe content, are input at keyboards 64 and stored in file 66. File 66 is merged at 68 with the file 56 of factor loadings in a format suitable for multiple linear regression analysis (70) which outputs regression statistics 72, a file 74 of regression coefficients and a file 76 of residuals. File 76 is merged at 78 with the original keyed-in data (file 66) to allow plotting (79) of measured properties against values predicted by the regression equation.

A spectrum for an unknown blend is taken up by program 80 which also uses files 58, 62 (respectively the inverses of the primary eigenvalues and the abstract factors) to calculate the factor loadings for each abstract factor needed to produce the spectrum, i.e. the factor loadings for the sampled portion of the unknown blend of each of the multiple pre-determined abstract factors. These loadings are stored in a file 82. Program 80 also utilizes the file 74 of pre-determined regression coefficients to calculate from the factor loadings a predicted value (83) for the selected parameter - Fe content.

The predicted value is compared (84) with related programmed set points comprising an optimum value (here, 62% Fe content) and/or an acceptable deviation range. If outside, instruction signals are transmitted for controlled adjustment of one or both feeders 14, 15 to adjust the Fe content of the blend.

The reproduced spectrum is saved (81) for later plotting by program 46 on the same axes as the original spectrum, thus providing a visual indication of goodness of fit. A statistical measure of the quality of the prediction may be achieved by program 86 which outputs 95% confidence intervals.

The contents of the following articles are incorporate herein by reference, for the purpose of explaining the application of factor analysis to problems of physical chemistry:

- H. H. Harmon, Modern Factor Analysis (University of Chicago Press, Chicago, 1976).
- P. H. Weiner, E. R. Malinowski and A. R. Levinstone, J. Phys. Chem. 74, 4537 (1970).
- P. H. Weiner, Chemtech, 321 (1977).
- E. R. Malinowski and D. G. Howery, Factor Analysis in Chemistry (Wiley, N.Y., 1980).

The factor analysis program may comprise FACTANAL, or one of a number of commercially available factor analysis packages (e.g. BMDP, SAS) suitably modified to take account of the number of samples and the number of measurements taken for each sample. FACTANAL is available from Program 320 Quantitative Chemistry Program Exchange, Indiana. University, Bloomington, Ind., U.S.A.

The multiple linear regression 70 may be carried out by means of the JSTAT software package (J. J. Deakin, JSTAT statistical computer program package, available through HP1000 Users' Group).

Figure 3:
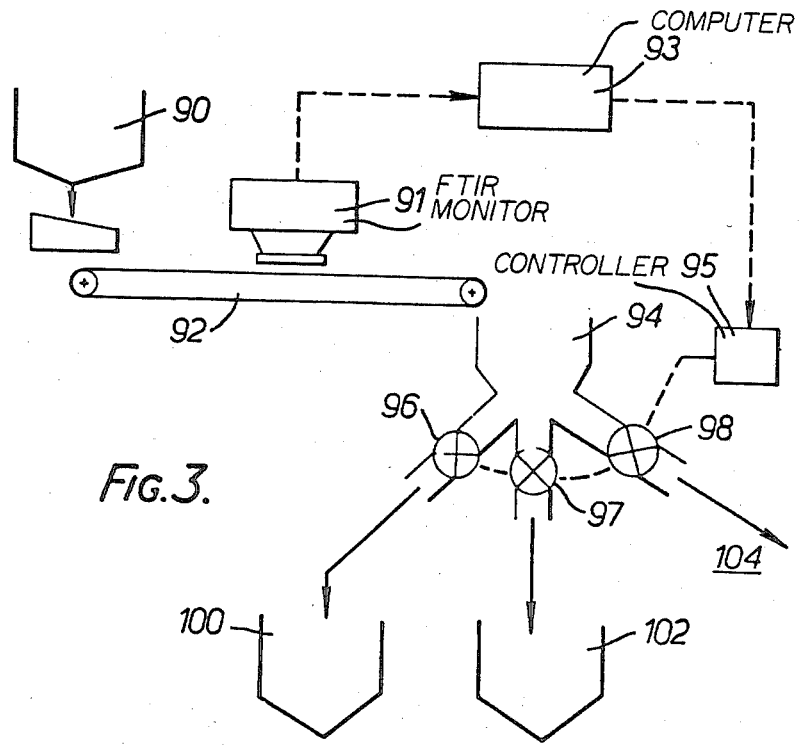
FIG. 3 is a diagram similar to FIG. 1 of diverter plant controlled according to the invention.

FIG. 3 schematically illustrates a further embodiment of the invention. By way of background, manganese dioxide ($MnO_2$) ore can be used for metallurgical purposes or for battery making depending on the molecular structure of the mineral phases present. Battery grade material is considerably more valuable. An FTIR spectrometer interfaced to a computer, equipped with software generally functioning according to the flow chart of FIG. 2, may be used to automatically divert run-of-mine ore to either a battery grade stockpile or a metallurgical grade stockpile using a correlation derived from battery tests of the ore. Simultaneously, the amount of gangue in the ore may be estimated and high gangue material diverted to a third stockpile for beneficiation or waste. In conventional practice, battery activity is repeatedly measured from prescribed large batches by manufacturing and discharging a small battery under standard conditions.

In the arrangement outlined in FIG. 3, run-of-mine $MnO_2$ ore is delivered from a hopper 90 along belt conveyor 92 to a diverter shute 94 with three selectively controllable gates 96, 97, 98 respectively to stockpiles for vernadite-rich battery active ore 100, pyrolusite-rich metallurgical grade ore 102, and to waste or beneficiation 104 in the case of low grade ore. Controller 95 for the gates is managed by a process control computer 93 which receives spectra from a FTIR monitor 91 periodically scanning ore on conveyor 92. In accordance with the invention, the computer is programmed to periodically estimate battery activity and gangue content for the ore from the FTIR spectra, to compare the estimates with various pre-programmed set points, and, responsive to the outcome of the comparisons, to determine through which gate the related batch ore is despatched.

The following examples illustrate the analytic application of the invention to the characterization of coal, the estimation of battery activity and elemental constituents of $MnO_2$ ore, the characterization of bauxite, and the estimation of particular properties of diesel fuel.

EXAMPLE 1

The standard characterized samples utilized to obtain the data points for factor analysis comprised a wide variety of 43 international coals used in commercial coke making and obtained from a number of countries.

Each series of measurements comprised an FTIR spectrum, obtained by the alkali halide pellet technique. In each case a sample of ground air-dried coal was added to a known amount of high purity caesium iodide in the agate capsule of a small vibratory mill. The mixture was milled, after which two pellets were pressed. Two hundred and seventy interferograms were signal-averaged and a primary spectrum then obtained, by Fourier transformation in the wavenumber range 4800–225 $cm^{-1}$, from which a reference spectrum of caesium iodide was subtracted to yield the coal spectrum. The instrument was continually purged with dry nitrogen. Spectra were obtained for both pellets and each coal was measured in duplicate giving a total of four standard spectra for each coal. Spectra were normalized to a selected coal concentration and the four spectra for each coal were averaged.

After baseline correction, spectral data were transferred to a Hewlett Packard HP1000 mini-computer for factor analysis.

The C-H stretching region, 3100 $cm^{-1}$ to 2800 $cm^{-1}$, of the spectra of the 43 coals, was digitised as 312 data points and subjected to factor analysis to derive a matrix of 13 abstract factors. The computer program, which was derived and modified from the aforementioned factor analysis program (FACTANAL), also calculated the associated loading matrices comprising the factor loadings of the abstract factors for each coal.

It was found that multiple linear regression of the loadings of the 13 abstract factors for each coal against the known values of selected and accepted coal properties produced a number of good correlations. Indeed it was surprising that such correlations existed despite the small region of spectrum studied. Close correlations, with correlation coefficients greater than 0.9, were obtained for mean maximum vitrinite reflectance, volatile matter content, hydrogen content, fluidity, and Hardgrove grindability index. Correlation coefficients in the range 0.8 to 0.9 were obtained for carbon content, ash content, and specific energy. Correlations for representative parameters are indicated in Table 1.

FTIR spectra obtained in like manner from suitably prepared test samples of 14 unknown coals or coal blends were then obtained. Factor loadings for the test samples of each of the derived factors were determined and regression coefficients, obtained by the multiple linear regression, utilized to calculate predicted values for each of the abovementioned parameters. On comparison of the predicted values with values obtained by conventional analytical techniques, it was found that, for properties such as ash, mineral matter, volatile matter, carbon, hydrogen, nitrogen and total sulphur content as well as $CO_2$ and specific energy, the predicted values were correct to the accuracy expected from the standard error of estimate found for the linear regression obtained for the known standard samples in most cases.

The time required to obtain a full analysis of an unknown coal, albeit at a lower level of accuracy than standard methods, was found to be about 2 hours, utilising only a single laboratory assistant.

EXAMPLE 2

It has also been found that the invention may be utilized to predict the properties of cokes made under standard conditions, from a number of coals. A surprising correlation was obtained for the microstrength index ($MSI_{600}$) of individual cokes made from 13 of the aforedescribed standard coals, together with 10 further cokes made from various blends of those 13 coals. These 23 coals and blends were subjected to factor analysis separately in the region 3100 to 2800 wavenumbers as before and it was found that seven abstract factors were required. Correlations were found with microstrength index and with various coke strength parameters, and with coke reactivity properties. Thus, knowledge of the infrared spectrum of the coal was able to give useful information about properties of the coke derived from that coal.

EXAMPLE 3

Figure 4:
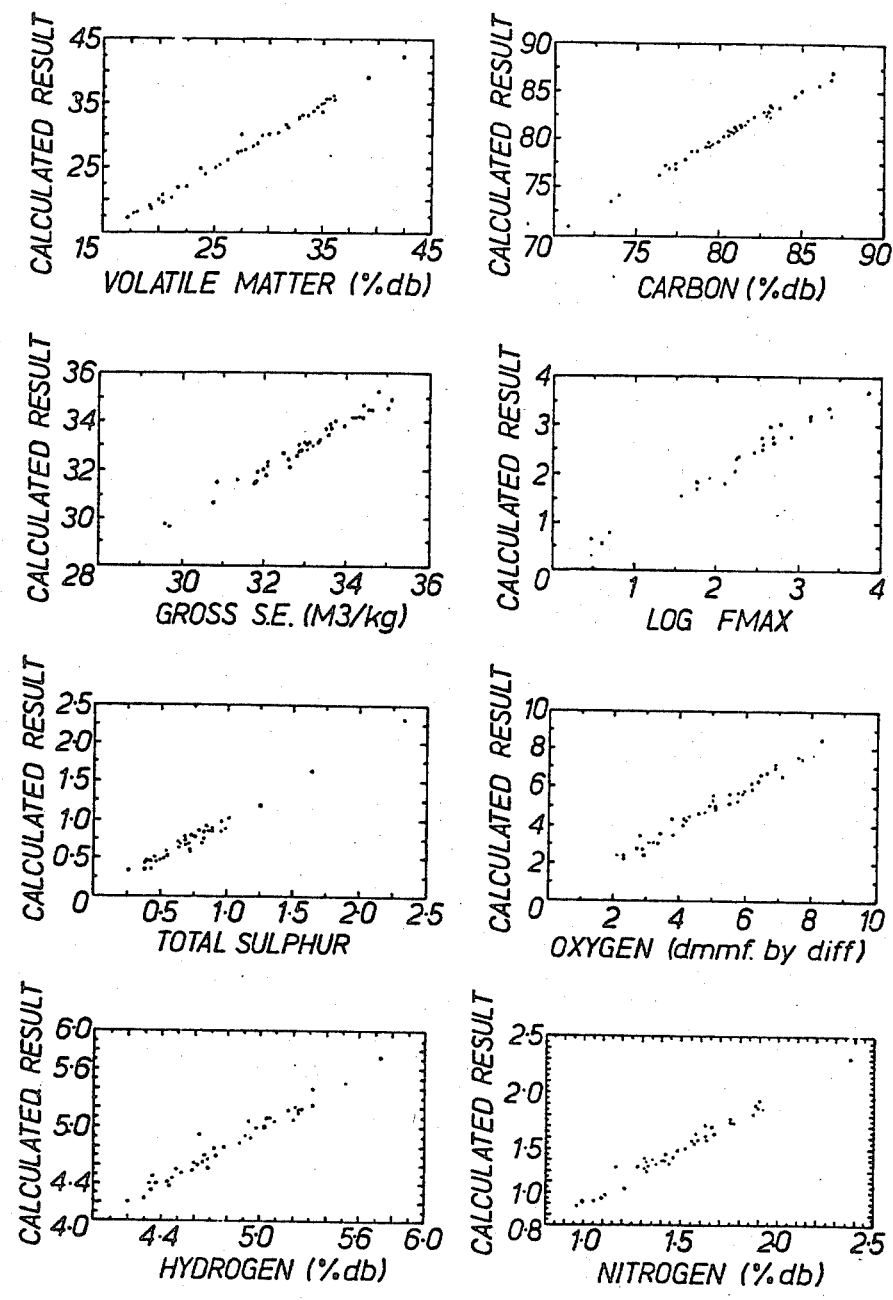
FIGS. 4 and 5 comprise correlation curves for chemical analysis (FIG. 4) and petrographic and ash analysis (FIG. 5) of a coal blend, plotted as the measured value against the value calculated from the respective regression equation.
Figure 5:
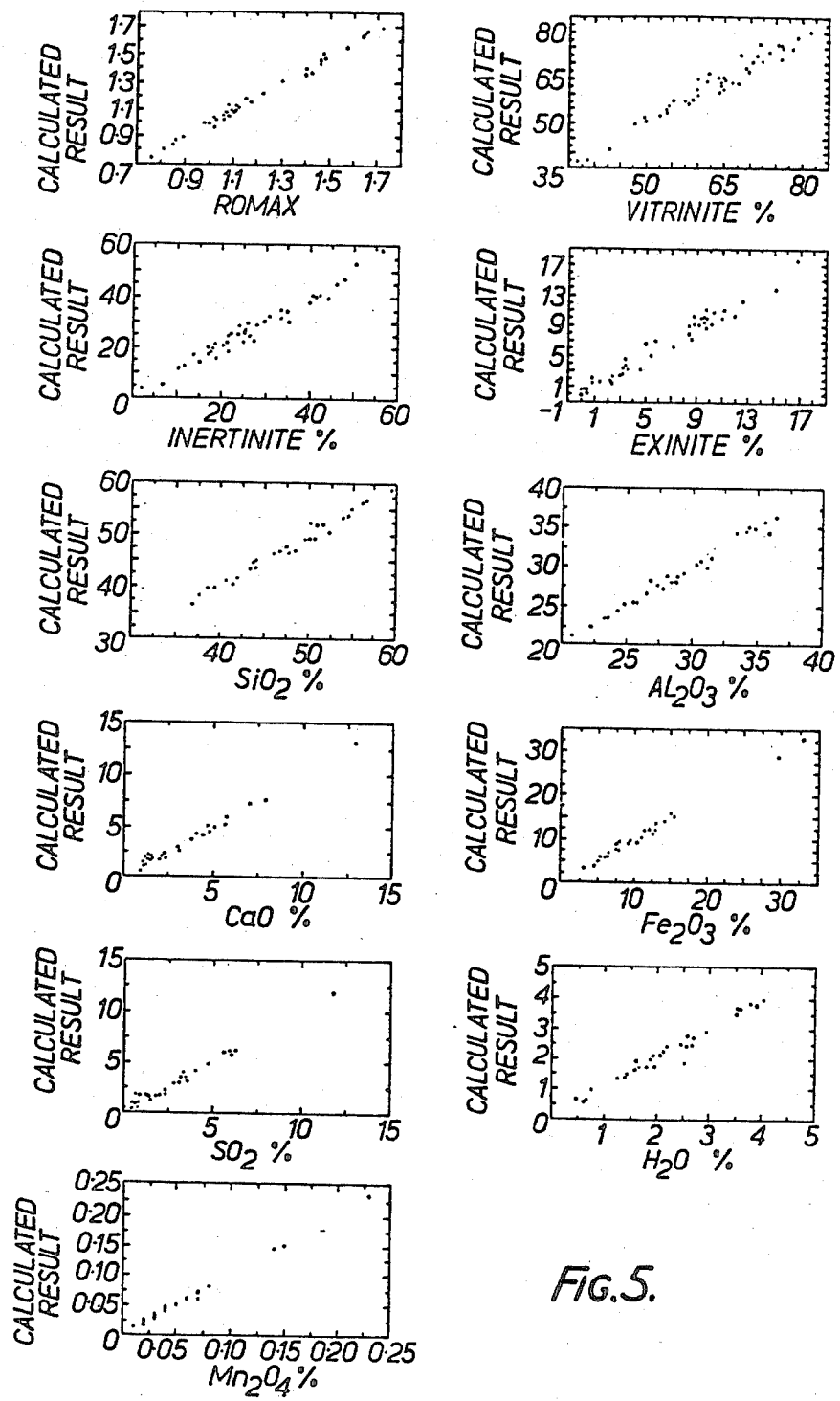

The steps of Example 1 were repeated except that, in this case, the spectral region selected for factor analysis was 2100 to 300 wavenumbers and comprised 1867 data points. 26 abstract factors proved necessary. The factor loadings for each of the coals were then related to measured coal properties using multiple linear regression methods as before, producing several close correlations. In the cases of some parameters, the correlation coefficient was markedly better than in Example 1, indicating that the choice of spectral region influences the accuracy achievable with predictions of a particular parameter. The results are set out in Table 2, in which both coefficients of determination and standard derivations are provided for each parameter for which a correlation was attempted. FIG. 4 shows the correlations for chemical analysis plotted as the measured value against the value calculated from the respective regression equation. FIG. 5 shows similar plots of the correlations for petrographic and ash analysis.

EXAMPLES 4,5,6

In addition to coal, the factor analysis technique was also applied to manganese dioxide ore, bauxite and diesel fuel. Different regions of the FTIR spectrum were chosen for each material with a view to including information on all major molecular structures present in the sample. These regions were, for manganese ore 822–320 $cm^{-1}$ (549 calibration points), for bauxite 1800–200 $cm^{-1}$ (1659 calibration points) and for diesel fuel 3100–2800 $cm^{-1}$ (311 calibration points). The results are given in Table 3. Again, close correlations were obtained with a wide variety of measured properties.

The calibration sets, especially that for diesel fuels, were rather smaller than would be used in practice and improvements in correlations could be expected if more samples were included in the base calibration set. The correlations obtained illustrate the advantage of this technique for the rapid characterization of materials. For example, the battery activity of manganese dioxide ore is routinely measured by a time-consuming method which involves preparation and discharge of a small battery under controlled conditions.

Correlations could not be obtained for a number of additional properties of diesel fuel including cloud point (ASTM D2500-81) and hydrocarbon types (ASTM D1319-77).

EXAMPLE 7.

The prediction of the properties of unknown samples was demonstrated for the restricted calibration set consisting of samples from a single coal mine. Correlations were obtained for ash and specific energy for various combinations of 90 samples (Table 4). The predictive ability of the correlations was tested by using them to estimate the ash and specific energy of a further 30 unknown samples, 10 each of the three types of product material, A-grade coal, C-grade coal, and fines. As shown in Table 4, various correlation equations were derived depending on which of the 90 samples was included in the calibration set. The quality of the correlations varied with the calibration set used and thus the accuracy of the predicted results varied in the same way.

Table 5 summarizes the results. Best results for the A and C coals were obtained with a calibration set consisting of all 90 calibration samples. A root mean square (RMS) difference between the measured and predicted results of 0.43% for ash was obtained. This result is approximately the error inherent in the ash measurement by combustion, and indicates that the FTIR method could produce results of the quality of conventional measurements, but in a much shorter time. Specific energy could not be estimated with the full calibration set because measured values were not available for the fine (F) samples. However, it could be estimated, with an RMS difference of 0.11 MJ/kg, for the combined A and C unknown samples using the A and C calibration set. The differences between measured and predicted values, when the other calibration sets were used, are consistent with the quality of the correlations as given in Table 4.

TABLE 1

| Coal Property | Correlation Coefficient |
| --- | --- |
| Reflectance (Ro max) | 0.99 |
| Volatile Matter (db %) | 0.99 |
| Hydrogen (db %) | 0.92 |
| Carbon (db %) | 0.87 |
| Ash (db %) | 0.78 |
| Specific Energy (MJ kg-1, db) | 0.82 |
| Fluidity (log F max) | 0.92 |
| Hardgrove Grindability Index | 0.97 |

TABLE 2

| Property | No. of samples | No. of factors | Range of values | No. of terms in regression equation | Coefficient of determination ($R^2$) | Standard deviation |
| --- | --- | --- | --- | --- | --- | --- |
| CHEMICAL ANALYSIS | | | | | | |
| Carbon (wt %, db) | 43 | 26 | 70.9–86.9 | 17 | 0.990 | 0.39 |
| Organic hydrogen (wt %, db) | 43 | 26 | 4.20–5.73 | 12 | 0.936 | 0.12 |

TABLE 2-continued

| Property | No. of samples | No. of factors | Range of values | No. of terms in regression equation | Coefficient of determination ($R^2$) | Standard deviation |
|---|---|---|---|---|---|---|
| Oxygen (wt %, dmmf, by diff.) | 43 | 26 | 2.11–8.30 | 11 | 0.957 | 0.41 |
| Nitrogen (wt %, db) | 43 | 26 | 0.96–2.37 | 10 | 0.907 | 0.09 |
| Total Sulphur (wt %, db) | 43 | 26 | 0.25–2.33 | 9 | 0.868 | 0.10 |
| Volatile matter (wt %, db) | 43 | 26 | 17.2–42.3 | 11 | 0.975 | 0.96 |
| Mineral matter (wt %, db) | 43 | 26 | 2.8–17.0 | 9 | 0.973 | 0.54 |
| Ash (wt %, db) | 43 | 26 | 2.5–16.2 | 14 | 0.985 | 0.42 |
| Specific energy (MJ/kg, db) | 43 | 26 | 29.58–35.10 | 7 | 0.935 | 0.39 |
| Fluidity (Log Fmax) | 29 | 11 | 0–4 | 2 | 0.251 | 0.93 |
| Hardgrove grindability index | 30 | 12 | 49–99 | 3 | 0.847 | 6.0 |
| PETROGRAPHIC ANALYSIS | | | | | | |
| Vitrinite reflectance (Ro max) | 42 | 26 | 0.76–1.72 | 15 | 0.988 | 0.04 |
| Vitrinite (vol %) | 43 | 26 | 36.6–81.4 | 8 | 0.905 | 4.1 |
| Inertinite (vol %) | 43 | 26 | 2.0–56.6 | 10 | 0.919 | 4.0 |
| Exinite (vol %) | 43 | 26 | 0.0–16.8 | 11 | 0.935 | 1.4 |

TABLE 3

| | Range of values | No. of terms in regression equation | Coefficient of determination ($R^2$) | Standard deviation |
|---|---|---|---|---|
| BAUXITE (37 samples, 16 factors, 1236–229 cm$^{-1}$) | | | | |
| Total alumina | 17–54 | 6 | 0.975 | 1.8 |
| Extractable alumina | 7–46 | 2 | 0.978 | 1.9 |
| Total silica | 1–24 | 12 | 0.987 | 0.7 |
| % $Fe_2O_3$ | 12–60 | 5 | 0.977 | 2.8 |
| Ignition loss | 4–29 | 4 | 0.938 | 1.9 |
| Total carbon | 0.15–0.64 | 11 | 0.893 | 0.04 |
| MANGANESE DIOXIDE ORE (22 samples, 12 factors, 822–320 cm$^{-1}$) | | | | |
| Battery activity | 70–120 | 6 | 0.892 | 4.7 |
| % Manganese | 44–57 | 4 | 0.955 | 0.82 |
| % Iron | 1–7 | 9 | 0.962 | 0.39 |
| % Silica | 1–13 | 7 | 0.962 | 0.61 |
| % Alumina | 1–7 | 3 | 0.821 | 0.43 |
| % Magnesia | 0–1 | 4 | 0.957 | 0.06 |
| DIESEL FUEL (17 samples, 7 factors, 3100–2800 cm$^{-1}$) | | | | |
| API gravity | 32.4–38.4 | 6 | 0.968 | 0.41 |
| Cetane Index | 46.6–53.0 | 7 | 0.979 | 0.43 |

TABLE 4

| Calibration set (No. of samples) | No. of factors | No. of terms in regression equation Ash | No. of terms in regression equation Specific energy | Ash (wt %, db) Coefficient of determination ($R^2$) | Ash (wt %, db) Standard deviation | Specific energy (MJ/kg, db) Coefficient of determination ($R^2$) | Specific energy (MJ/kg, db) Standard deviation |
|---|---|---|---|---|---|---|---|
| A, C, F (90) | 33 | 16 | — | 0.997 | 0.67 | ND | ND |
| A, C (60) | 23 | 13 | 13 | 0.997 | 0.23 | 0.995 | 0.10 |
| A (30) | 13 | 5 | 3 | 0.948 | 0.25 | 0.870 | 0.13 |
| C (30) | 11 | 5 | 5 | 0.984 | 0.37 | 0.969 | 0.19 |
| F (30) | 13 | 5 | — | 0.987 | 1.10 | ND | ND |

TABLE 5

Summary of results for the characterization of unknown A, C and F-grade coals from a single coalmine, using correlations obtained from factor analysis of FTIR spectra. A = A-grade coal (ash 12-15%, db), C = C-grade coal (ash 16-25%, db), F = fine material (ash >25%, db).

| Calibration set | Unknowns | RMS Difference Ash (wt %, db) | Specific Energy (MJ/kg) |
| --- | --- | --- | --- |
| A, C, F (90 samples) | A, C, F | 1.05 | — |
|  | A, C | 0.43 | — |
|  | A | 0.47 | — |
|  | C | 0.38 | — |
|  | F | 1.72 | — |
| A, C (60 samples) | A, C | 0.50 | 0.11 |
|  | A | 0.52 | 0.09 |
|  | C | 0.48 | 0.13 |
| A (30 samples) | A | 0.59 | 0.48 |
| C (30 samples) | C | 0.58 | 0.31 |
| F (30 samples) | F | 2.17 | — |

We claim:

1. A method of handling, as bulk material, a substance which is one member of a class of multi-component substances having identifiable common properties, said method comprising:
   subjecting successive test samples of said substance to a series of measurements which provide multiple data points influenced by at least one selected parameter;
   calculating, from the data points, factor loadings for the respective test sample for each of multiple predetermined abstract factors;
   calculating a predicted value for said at least one selected parameter for the respective test sample from said factor loadings and predetermined regression coefficients;
   comparing said predicted value of said at least one selected parameter with at least one corresponding predetermined set point;
   controlling the constitution and/or disposition of said substance in response to said comparison;
   wherein said regression coeeficients have been obtained by correlating known values of said at least one selected parameter for standard samples of each of multiple substances of said class with factor loadings obtained by factor analysis of multiple data points which were obtained by subjecting said standard samples to said series of measurements and wherein said abstract factors are obtained by said factor analysis.

2. The method according to claim 1, wherein said substance being handled is being blended from bulk supplies of other substances of said class, and wherein said controlling comprises controlling the relative proportions of said other substances in said blend.

3. The method according to claim 1, wherein said controlling comprises determining in which of plural alternative directions the substance is despatched.

4. The method according to claims 1, 2 or 3, wherein said substance is coal.

5. The method according to claims 1, 2 or 3, wherein said substance is an ore of a specific metal selected from the group consisting of manganese ore and bauxite.

6. The method according to claims 1, 2 or 3, wherein said series of measurements are such that said measurements and said at least one selected parameter are strongly related to a common set of fundamental chemical and structural constituents of the substance.

7. The method according to claim 6, wherein said series of measurements comprise an infrared spectrum.

8. The method according to claims 1, 2 or 3, wherein said correlation is performed by multiple linear regression of the factor loadings, obtained by said factor analysis, against said known values.

9. The method according to claims 1, 2 or 3, wherein said at least one selected parameter is a physical property variable between substances of said class.

10. An apparatus for handling, as bulk material, a substance which is one member of a class of multi-component substances having identifiable common properties, said apparatus comprising:
    measurement means for subjecting successive test samples of said substances to a series of measurements which provide multiple data points influenced by at least one selected parameter;
    determining means for calculating, from the data points, the factor loadings for the respective test samples for each of multiple predetermined abstract factors;
    storage means for storing predetermined regression coefficients;
    calculation means for calculating a predicted value for said at least one selected parameter for the respective test sample from said regression coefficients and said factor loadings;
    comparison means for comparing said predicted value of said at least one selected parameter with at least one corresponding predetermined set point;
    control means, coupled to and responsive to said comparison means, for controlling the constitution and/or disposition of said substances;
    wherein said regression coefficients have been determined by correlating known values of said at least one selected parameter for standard samples of each of multiple substances of said class with factor loadings obtained by factor analysis of multiple data points which were obtained by subjecting said standard samples to said series of measurements, and wherein said abstract factors are obtained by said factor analysis.

11. The apparatus according to claim 10, wherein said control means comprises a blending plant for blending said substance from bulk supplies of other substances of said class, said plant responsive to said comparison means to control the relative proportions of said other substances in the blend.

12. The apparatus according to claim 10, wherein said control means comprises a diverter plant, responsive to said comparison means, to determine in which of plural alternate directions the substances is despatched.

13. The apparatus according to claims 10, 11 or 12, wherein said measurement means comprises a spectrometer such that said measurements and said at least one selected parameter are strongly related to a common set of fundamental chemical and structural constituents of said substance.

14. The apparatus according to claim 13, wherein said series of meaurements comprise an infrared spectrum.

15. The apparatus according to claims 10, 11 or 12 wherein said determining, storage, calculation and comparison means comprise a programmed computer.

* * * * *